United States Patent [19]

Gottinger

[11] 4,403,987
[45] Sep. 13, 1983

[54] DEVICE FOR AIDING INJECTION OF A HYPODERMIC SYRINGE

[75] Inventor: John G. Gottinger, Fond du Lac, Wis.

[73] Assignee: Gottinger Company, Inc., Fond du Lac, Wis.

[21] Appl. No.: 342,150

[22] Filed: Jan. 25, 1982

[51] Int. Cl.³ .............................................. A61M 5/00
[52] U.S. Cl. ...................................... 604/115; 604/134
[58] Field of Search ............... 128/215, 218 R, 218 F, 128/218 A, 214 R, DIG. 6; 604/115, 134, 93, 48, 131

[56] References Cited

U.S. PATENT DOCUMENTS 2,266,230 12/1941 Mazzeo et al. ................. 128/214 R
2,266,231 12/1941 Mazzeo et al. ................. 128/214 R
2,660,169 11/1953 Malm .............................. 128/218 F
2,859,749 11/1958 Johnson ......................... 128/218 F Primary Examiner—John D. Yasko

[57] ABSTRACT

An injection aid for supporting a hypodermic syringe and for facilitating injection of the needle of the syringe into a limb. The apparatus includes a syringe supporting member and a pair of guide rods for supporting the syringe supporting member for slideable movement between a first position wherein a needle supported by the syringe supporting member is retracted from the limb and an injecting position. A pair of spaced apart generally parallel support rods are also provided. The rearward ends of the support rods being adapted to rest on the limb and are integrally joined to the guide rods and for supporting the guide rods. The support rods include forward ends for pinching flesh therebetween to cause the flesh adjacent the syringe needle to pucker.

12 Claims, 2 Drawing Figures

DEVICE FOR AIDING INJECTION OF A HYPODERMIC SYRINGE

FIELD OF THE INVENTION

The invention relates to a new and useful device to assist diabetics in injecting insulin and to improvements in holders for hypodermic syringes designed particularly for use in self administration of hypodermic injections and including the provision of means for pinching or puckering the flesh and for supporting the syringe for penetration.

BACKGROUND PRIOR ART

A person who is diabetic may be required to take at least one self administered insulin injection each day. A proper injection requires the patient to pinch or pucker the flesh while also supporting and manipulating the syringe. It is also necessary, once the needle is inserted, to withdraw the plunger slightly to insure that the needle is not injected into a vein or artery. It will be appreciated that properly positioning of the syringe, pinching the flesh and manipulating the plunger is particularly difficult when the injection is made into an arm, and where the patient has only one hand available for pinching the flesh and for manipulation of the hypodermic syringe.

Various prior art devices have been developed to support hypodermic syringes and in an effort to make such injections easier. See, for example, the Collins U.S. Pat. No. 2,252,398, issued Oct. 10, 1950; the Kayden U.S. Pat. No. 2,295,849, issued Sept. 15, 1942; and the Weese U.S. Pat. No. 3,324,854, issued June 13, 1967.

Attention is also directed to the Harris U.S. Pat. No. 4,185,627, issued Jan. 29, 1980 and the Harris Pat. No. 4,223,673, issued Sept. 23, 1980.

SUMMARY OF THE INVENTION

The present invention provides an apparatus for supporting a hypodermic syringe and for facilitating injection of the needle of the hypodermic syringe into an arm or leg. The apparatus includes a syringe supporting member and guide means for supporting that member for movement between a first position wherein a needle supported on the syringe supporting member is retracted and a second or injecting position. The means for supporting includes a pair of guide rods for supporting the syringe supporting member for slideable movement between the first position and the injecting position, and means for supporting the guide means and for pinching the flesh adjacent the syringe needle. The means for supporting the guide rods includes a pair of spaced apart generally parallel support rods having rearward ends adapted to rest on the arm or leg and being integrally joined to the guide means, and the support rods including forward ends for pinching flesh therebetween to cause the flesh adjacent the syringe needle to pucker. Spring means are also provided for resiliently biasing forward ends of the support rods together.

In a preferred embodiment of the apparatus of the invention the means for supporting the guide means further includes clamping means for clampingly engaging the limb, the clamping means including a pair of arms adapted to be positioned on opposite sides of the limb and to clampingly engage the limb, one of the arms being integrally joined to a forward end of one of the support rods, and the other of the arms being integrally joined to a forward end of the other of the support rods.

In a preferred form of the invention the rearward end of one of the guide rods is integrally joined to the rearward end of one of the support rods by a first rod extending transversely to the guide rod and the rearward end of the other guide rod is integrally joined to the rearward end of the other of the support rods by a second rod.

Another feature of a preferred form of the invention is that the rearward ends of the guide rods are spaced above the rearward ends of the spaced parallel rods and the forward ends of the guide rods are closely adjacent the forward ends of the support rods.

In a preferred embodiment of the invention the guide rods and the spaced parallel support rods are comprised of a one piece continuous elongated member.

Another feature of the invention is the provision of resilient means for biasing the syringe supporting member toward the injecting position, the resilient means including springs surrounding the guide rods.

One of the principal features of the invention is that it provides an improved syringe holder which relieves the operator of manual support of the syringe during the injection, thereby making it easier for the operator to manipulate the syringe plunger.

Another feature of the invention is that it provides a means for properly pinching or puckering the flesh in the area of penetration of the needle and relieves the patient of attempting to both pucker the flesh and manipulate the syringe and the syringe plunger.

Another feature of the apparatus embodying the invention is that it is useful for supporting the syringe for an injection in either an arm or leg.

Various other features and advantages of the invention will be apparent by reference to the following description of a preferred embodiment, to the claims, and to the drawings.

Figure 1:
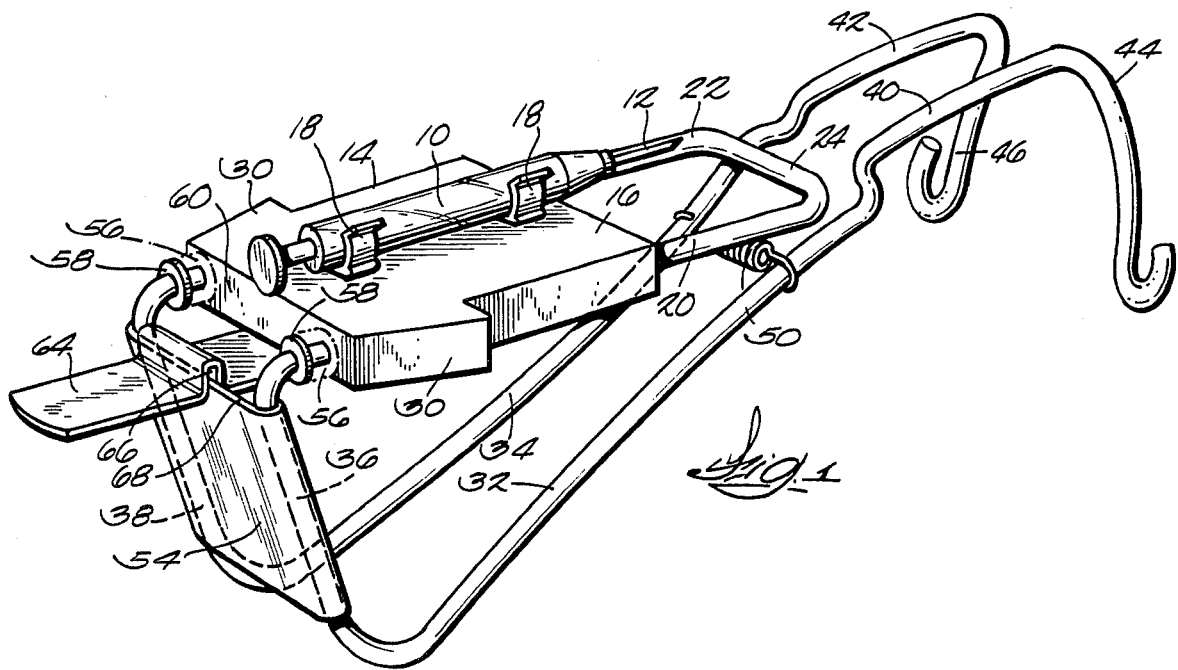
FIG. 1 is a perspective view of apparatus for supporting a hypodermic syringe embodying the invention.

Before describing at least one of the embodiments of the invention in detail, it is to be understood that the invention is not limited in its application to the details of construction and to the arrangements of components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF A PREFERRED EMBODIMENT

Figure 2:
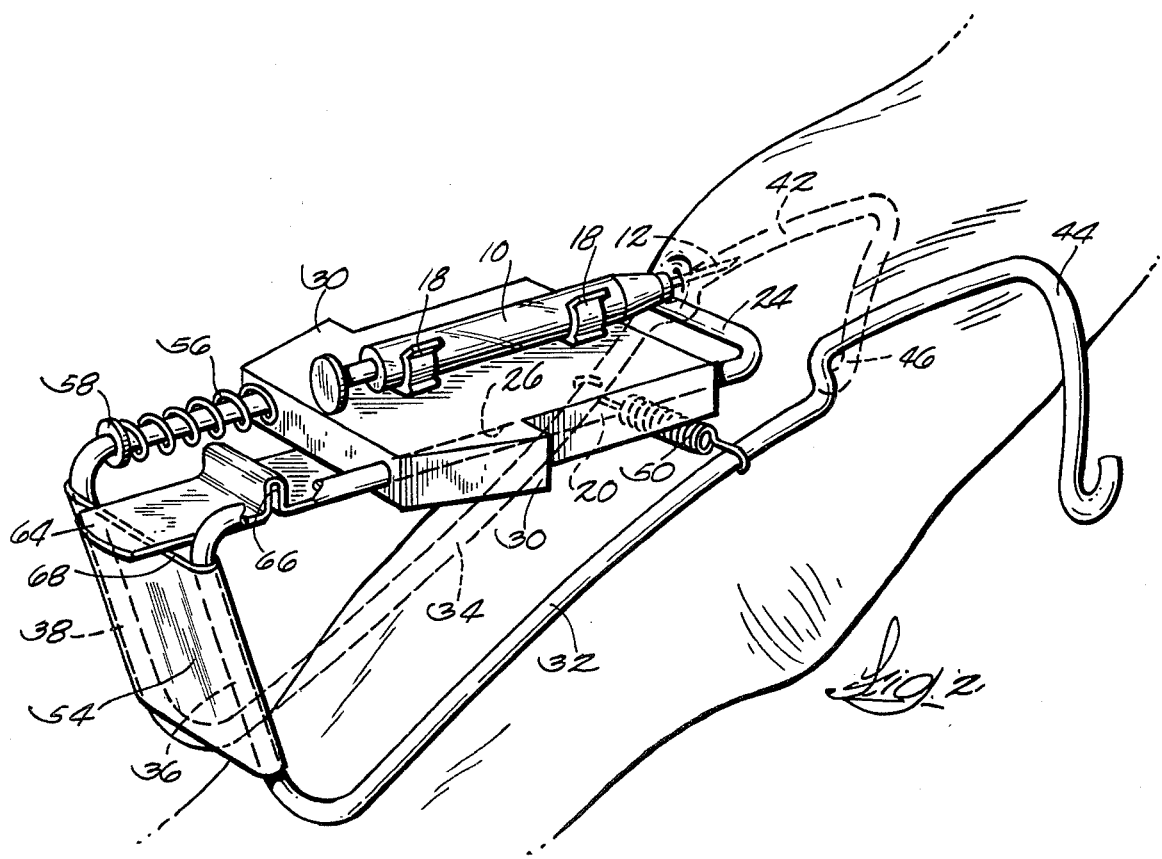
FIG. 2 is a view similar to FIG. 1 and showing the apparatus clampingly engaging a patient's arm and with the syringe in an injection position.

Illustrated in FIG. 1 is an apparatus embodying the invention and for use in supporting a hypodermic syringe 10 having a needle 12. The apparatus of the invention is particularly suited for use by diabetics for self injection of insulin, and may be used for injections in either an arm or leg. The apparatus includes a means for releasably supporting a hypodermic syringe 10 for movement between a retracted position as illustrated in FIG. 1 and an injection position illustrated in FIG. 2 wherein the needle 12 of the syringe 10 is inserted into the flesh. The means for supporting the syringe 10 includes a slide plate or syringe supporting member 14 having a generally planar upper surface 16 and a pair of spring clips 18 supported by the plate 14 and extending upwardly from the upper surface 16. The spring clips 18 are adapted to releasably clampingly engage opposite ends of the syringe 10.

Means are further provided for supporting the slide plate 14 for slidable movement between a retracted position and a needle insertion position. More particularly, the plate is movable from a position illustrated in FIG. 1 wherein the syringe 10 on the slide plate is supported such that the needle 12 is retracted and a second position illustrated in FIG. 2 wherein the needle is inserted. This means for supporting the plate 14 includes a pair of parallel, spaced apart guide rods 20 and 22, the guide rods 20 and 22 being joined at their forward ends by an integral connecting rod 24. The plate 14 includes a pair of parallel spaced bores 26 extending longitudinally through the plate 14 and adjacent its sides or lateral edges, the bores 26 slidably housing the guide rods 20 and 22 such that the plate 14 is freely slidable along the guide rods.

While in the illustrated construction the slide plate 14 includes bores 26 for housing the guide rods 20 and 22, in other arrangements the plate 14 could be provided with grooves cut in its lower surface for housing the guide rods.

In the illustrated construction, the slide plate 14 for supporting the syringe also includes a pair of flanges 30 extending laterally from its opposite edges and intended to permit the operator to grip the slide plate 14 so that it may be moved from its forward position to a rearward, retracted position.

Means are further provided for firmly supporting the plate 14 on the patient's arm or leg and for restricting movement of the slide plate and the syringe with respect to that arm or leg. This means for supporting comprises a clamp means for clampingly engaging the arm or leg and a means for pinching or puckering the flesh in the region adjacent the needle 12 and for causing the flesh to be puckered or raised in the area of injection so that the needle 12 can be easily inserted into the flesh and such that the needle does not hit a vein or artery. More particularly, the clamping means includes a pair of rods 32 and 34 supported in generally parallel relation and beneath the guide rods 20 and 22, respectively. The rods 32 and 34 are adapted to rest on the patient's arm or leg and to extend generally parallel to the arm or leg. The rod 32 is integrally joined to the rearward end of the guide rod 20 by a generally vertical rod portion 36, and the adjacent rod 34 is integrally joined at the rearward end to a rearward end of the guide rod 22 by a generally vertical rod portion 38. The parallel rods 32 and 34 also each include forward portions 40 and 42, respectively, extending forwardly beyond the forward ends of the guide rods 20 and 22. These forwardly extending rod portions 40 and 42 provide pinch bars and are particularly shaped so as to comprise a means for pinching a portion of the flesh of the arm or leg to cause that flesh to pucker in the area adjacent the needle 12 of the syringe 10. The forward ends of the pinch bars 40 and 42 are integrally joined to downwardly extending rod portions or clamping arms 44 and 46, respectively, which are adapted to firmly engage opposite sides of the arm or leg. The downwardly extending clamping arms 44 and 46 are curved so that they can conveniently surround a portion of the arm or leg. In a preferred form of the invention, the pinch bars 40 and 42 and the clamping arms 44 and 46 can be covered or coated with a silicone nonsplitubing material so that the pinch bars 40 and 42 can engage the skin and pinch or pucker the flesh between the pinch bars.

Means are also provided for biasing the pinch bars 40 and 42 and the clamping arms 44 and 46 toward one another to facilitate a firm engagement of the syringe supporting device with the patient's arm or leg. While various means could be provided for clamping these members together, in the illustrated arrangement it includes a coil spring member 50 having opposite ends connected to the rods 32 and 34 adjacent their forward ends and tending to force the forward ends of rods 32 and 34 toward one another.

In a preferred form of the invention, the guide rods 20 and 22 and the syringe support plate 14 slope downwardly from their rearward ends toward the rearward ends of the pinch bars 40 and 42 and such that the needle 12 of the syringe 10 supported by the support plate 14 can be injected into the flesh held between the pinch bars 40 and 42 and such that the syringe will be supported at a proper angle to facilitate the insertion of the needle 12.

Means are also provided for fixing the rearward ends of the rods 32 and 34 in spaced apart generally parallel relation and the rearward ends of the guide rods 20 and 22 in fixed spaced apart relation. While various means could be provided, in the illustrated construction this means includes a plate 54 having opposite generally vertical edges which clampingly engage the vertical rod portions 36 and 38.

Means are also provided for biasing the slide plate 14 and the syringe 10 toward a needle injection position, this means including a pair of compression springs 56, one spring 56 surrounding a rearward end of the guide rod 22. The rearward end of this spring 56 is supported by a washer or disc 58 fixed to the rearward end of the guide rod 22 and surrounding the guide rod. The spring 56 is compressed between the disc 58 and the rearward surface 60 of the slide plate 14. A similar compression spring 56 surrounds the guide rod 20 and is compressed between a disc 58 and the rearward surface 60 of the plate 14.

Means are also provided for releasably holding the slide plate 14 in a retracted position as illustrated in FIG. 1 and with the springs 56 compressed. In the illustrated arrangement, the means for holding the plate 14 in a retracted position includes a resilient metal lever 64 having a forward end secured to the lower surface of the slide plate 14 and having a portion extending rearwardly from the slide plate. The lever 64 is formed so as to include a downwardly opening groove 66 intermediate its opposite ends, the groove 66 being adpated to house the upper edge 68 of the plate 54 when the slide plate 14 is in its rearward retracted position. The lever 64 is comprised of a resilient material such that the rearward end of the lever can be raised whereby the groove 66 will release the upper edge 68 of the plate 54 and the compression springs 56 can cause forward movement of the slide plate 14 and the syringe supported on the plate.

In operation of the injector aid of the invention, it provides complete support and proper positioning of the syringe during injection of the needle into the flesh, and also includes means for providing the proper pinching or puckering of the flesh in the area of insertion of the needle. Accordingly, the patient is permitted free use of his or her free hand to properly operate the plunger. Additionally, while the injector has been described as being useful for self injection of insulin in an arm, the injector aid can also be used to clampingly engage a leg for injection into a leg.

Various features of the invention are set forth in the following claims.

I claim:

1. Apparatus for supporting a hypodermic syringe to facilitate injection of the needle of the hypodermic syringe into a limb, the apparatus comprising
    a syringe supporting member having a syringe supporting surface adapted to support a syringe,
    guide means for supporting the syringe supporting member for movement between a first position wherein the needle of the syringe is retracted from the limb and an injecting position, said means for supporting including a pair of guide rods for supporting said syringe supporting member for slideable movement between said first position and said injecting position, and
    means for supporting said guide means on the limb and for pinching the flesh adjacent the syringe needle, said means for supporting said guide means including a pair of spaced apart generally parallel support rods having rearward ends adapted to rest on the limb and being integrally joined to said guide means, and said support rods including forward ends for pinching flesh therebetween to cause the flesh adjacent the syringe needle to pucker, and spring means for resiliently biasing said forward ends of said support rods together so as to cause said support rods to pinch the flesh therebetween.

2. Apparatus as set forth in claim 1 wherein said means for supporting said guide means further includes clamping means for clampingly engaging the limb, said clamping means including arms adapted to be positioned on opposite sides of the limb and to clampingly engage the limb, one of said arms being integrally joined to said forward end of one of said support rods, and the other of said arms being integrally joined to said forward end of the other of said support rods.

3. Apparatus as set forth in claim 1 wherein said guide rods each include a forward end and a rearward end, and wherein said rearward end of one of said guide rods is integrally joined to said rearward end of one of said support rods by a first rod portion extending transversely to said one of said guide rods and wherein said rearward end of the other of said guide rods is integrally joined to said rearward end of the other of said support rods by a second rod portion.

4. Apparatus as set forth in claim 1 and wherein said guide rods each include a forward end and a rearward end and wherein said rearward ends of said guide rods are spaced from said rearward ends of said spaced parallel rods and wherein said forward ends of said guide rods are closely adjacent said forward ends of said support rods.

5. Apparatus as set forth in claim 1 wherein said guide rods and said spaced parallel support rods are comprised of a one piece continuous elongated member.

6. Apparatus as set forth in claim 1 and further including means for fixing said rearward ends of said support rods in spaced apart relation.

7. Apparatus as set forth in claim 6 wherein said guide rods include forward ends and rearward ends and wherein said means for fixing provides means for fixedly supporting said rearward ends of said guide rods in parallel spaced apart relation.

8. Apparatus as set forth in claim 7 and further including a transverse rod integrally joining said forward ends of said guide rods.

9. Apparatus as set forth in claim 1 and further including resilient means for biasing said syringe supporting member toward said injecting position.

10. Apparatus as set forth in claim 9 and wherein said resilient means includes a coil spring surrounding one of said guide rods.

11. Apparatus as set forth in claim 10 wherein said guide rods include forward ends and rearward ends, wherein said guide means includes a transverse member positioned adjacent said rearward ends of said guide rods and fixedly supporting said guide rods in spaced apart relation, and further including means for releasably restraining said syringe supporting member in said first position.

12. Apparatus as set forth in claim 11 wherein said means for releasably restraining includes a lever having a forward end fixed to said syringe supporting member and a rearward end including means for releasably engaging said transverse member, said lever restraining said syringe supporting member in said first position when said rearward end of said lever engages said transverse member.

* * * * *